United States Patent [19]

Lam

[11] Patent Number: 5,649,952

[45] Date of Patent: *Jul. 22, 1997

[54] EXPANDABLE STENTS AND METHOD FOR MAKING SAME

[75] Inventor: Sharon S. Lam, San Jose, Calif.

[73] Assignee: Advanced Cardiovascular Systems, Inc., Santa Clara, Calif.

[*] Notice: The term of this patent shall not extend beyond the expiration date of Pat. No. 5,569,295.

[21] Appl. No.: 672,729

[22] Filed: Jun. 28, 1996

Related U.S. Application Data

[62] Division of Ser. No. 454,599, May 31, 1995, Pat. No. 5,569,295, which is a continuation of Ser. No. 396,886, Mar. 1, 1995, abandoned, which is a continuation of Ser. No. 175,214, Dec. 28, 1993, abandoned.

[51] Int. Cl.$^6$ ................................................ A61M 29/00
[52] U.S. Cl. ............................. 606/198; 606/195; 623/1; 623/12
[58] Field of Search ............................ 606/108, 191, 606/194, 195, 198, 200; 128/898, 899; 623/1, 12

[56] References Cited

U.S. PATENT DOCUMENTS

| | | |
|---|---|---|
| 3,105,492 | 10/1963 | Jeckel . |
| 3,657,744 | 4/1972 | Ersek . |
| 3,868,956 | 3/1975 | Alfidi et al. . |
| 3,993,078 | 11/1976 | Bergentz et al. . |
| 4,130,904 | 12/1978 | Whalen . |

(List continued on next page.)

FOREIGN PATENT DOCUMENTS

| | | |
|---|---|---|
| 0408245 | 1/1991 | European Pat. Off. . |
| 0428479 | 5/1991 | European Pat. Off. . |
| 36 40 745 | 6/1987 | Germany . |
| 57-89859 | 6/1982 | Japan . |
| 2 135 585 | 9/1984 | United Kingdom . |
| 08901798 | 3/1989 | WIPO . |
| 8908433 | 9/1989 | WIPO . |

OTHER PUBLICATIONS

Dotter, Charles T.: Transluminally Placed Coilspring Endarterial Tube Grafts, pp. 329–332, Sep.–Oct./1969, *Investigative Radiology*.

C.R. Bard: PE Plus Peripheral Balloon Dilatation Catheter, Aug./1985, *CR Bard, Inc.*.

Duprat et al.: Flexible Balloon–Expanded Stent for Small Vessels, pp. 276–278, 1987, *Radiology Journal*.

Maass et al.: Radiological Follow–up of Transluminally Inserted Vascular Endoprostheses: An Experimental Study Using Expanding Spirals, pp. 659–663, 1984, *Radiology Journal*.

Palmaz et al.: Expandable Intraluminal Graft: A Preliminary Study, pp. 73–77, 1985, *Radiology Journal*.

Wright et al.: Percutaneous Endovascular Stents: An Experimental Evaluation, 69–72, 1985, *Radiology Journal*.

Dotter: Transluminal Expandable Nitinol Coil Stent Grafting: Preliminary Report, pp. 259–260, Apr./1983, *Radiology Journal*.

Cragg et al.: Non–Surgical Placement of Arterial Endoprostheses: A New Technique Using Nitinol Wire, pp. 261–263, Apr./1983, *Radiology Journal*.

*Primary Examiner*—William Lewis
*Attorney, Agent, or Firm*—Fulwider Patton Lee & Utecht, LLP

[57] ABSTRACT

The invention is directed to an expandable stent for implantation in a body lumen, such as an artery. The stent consists of a plurality of radially expandable cylindrical elements generally aligned on a common longitudinal stent axis and interconnected by one or more interconnecting members placed so as to limit longitudinal contraction during radial expansion. The individual radially expandable cylindrical elements are formed in an irregular serpentine pattern designed to expand evenly under radial stress, and maximize the overall radial expansion ratio.

10 Claims, 3 Drawing Sheets

U.S. PATENT DOCUMENTS

| | | |
|---|---|---|
| 4,140,126 | 2/1979 | Choudhury . |
| 4,159,719 | 7/1979 | Haerr . |
| 4,323,071 | 4/1982 | Simpson et al. . |
| 4,332,254 | 6/1982 | Lundquist . |
| 4,439,185 | 3/1984 | Lundquist . |
| 4,468,224 | 8/1984 | Enzmann et al. . |
| 4,503,569 | 3/1985 | Dotter . |
| 4,512,338 | 4/1985 | Balko et al. . |
| 4,516,972 | 5/1985 | Samson . |
| 4,531,933 | 7/1985 | Norton et al. . |
| 4,538,622 | 9/1985 | Samson et al. . |
| 4,553,545 | 11/1985 | Maass et al. . |
| 4,554,929 | 11/1985 | Samson et al. . |
| 4,560,374 | 12/1985 | Hammerslag . |
| 4,569,347 | 2/1986 | Frisbie . |
| 4,571,240 | 2/1986 | Samson et al. . |
| 4,572,186 | 2/1986 | Gould et al. . |
| 4,580,568 | 4/1986 | Gianturco . |
| 4,616,652 | 10/1986 | Simpson . |
| 4,619,246 | 10/1986 | Molgaard-Nielsen et al. . |
| 4,649,922 | 3/1987 | Wiktor . |
| 4,650,466 | 3/1987 | Luther . |
| 4,655,771 | 4/1987 | Wallsten . |
| 4,665,918 | 5/1987 | Garza et al. . |
| 4,681,110 | 7/1987 | Wiktor . |
| 4,706,671 | 11/1987 | Weinrib . |
| 4,732,152 | 3/1988 | Wallsten et al. . |
| 4,733,665 | 3/1988 | Palmaz . |
| 4,739,762 | 4/1988 | Palmaz . |
| 4,740,207 | 4/1988 | Kreamer . |
| 4,748,982 | 6/1988 | Horzewski et al. . |
| 4,748,986 | 6/1988 | Morrison et al. . |
| 4,760,849 | 8/1988 | Kropf . |
| 4,762,128 | 8/1988 | Rosenbluth . |
| 4,768,507 | 9/1988 | Fischell . |
| 4,771,777 | 9/1988 | Horzewski . |
| 4,776,337 | 10/1988 | Palmaz . |
| 4,790,315 | 12/1988 | Mueller, Jr. et al. . |
| 4,795,458 | 1/1989 | Regan . |
| 4,800,882 | 1/1989 | Gianturco . |
| 4,830,003 | 5/1989 | Wolff et al. . |
| 4,848,343 | 7/1989 | Wallsten et al. . |
| 4,856,516 | 8/1989 | Hillstead . |
| 4,870,966 | 10/1989 | Dellon et al. . |
| 4,877,030 | 10/1989 | Beck et al. . |
| 4,878,906 | 11/1989 | Lindemann et al. . |
| 4,886,062 | 12/1989 | Wiktor . |
| 4,892,539 | 1/1990 | Koch . |
| 4,893,623 | 1/1990 | Rosenbluth . |
| 4,907,336 | 3/1990 | Gianturco . |
| 4,913,141 | 4/1990 | Hillstead . |
| 4,922,905 | 5/1990 | Strecker . |
| 4,923,464 | 5/1990 | DiPisa, Jr. . |
| 4,950,227 | 8/1990 | Savin et al. . |
| 4,969,458 | 11/1990 | Wiktor . |
| 4,969,890 | 11/1990 | Sugita et al. . |
| 4,986,831 | 1/1991 | King et al. . |
| 4,990,155 | 2/1991 | Wilkoff . |
| 4,994,071 | 2/1991 | MacGregor . |
| 4,998,539 | 3/1991 | Delsanti . |
| 5,002,560 | 3/1991 | Machold . |
| 5,007,926 | 4/1991 | Derbyshire . |
| 5,015,253 | 5/1991 | MacGregor . |
| 5,019,085 | 5/1991 | Hillstead . |
| 5,019,090 | 5/1991 | Pinchuk . |
| 5,026,377 | 6/1991 | Burton et al. . |
| 5,034,001 | 7/1991 | Garrison et al. . |
| 5,035,706 | 7/1991 | Giantureo et al. . |
| 5,037,377 | 8/1991 | Alonso . |
| 5,037,392 | 8/1991 | Hillstead . |
| 5,037,427 | 8/1991 | Harada et al. . |
| 5,041,126 | 8/1991 | Gianturco . |
| 5,059,211 | 10/1991 | Stack et al. . |
| 5,061,273 | 10/1991 | Yock . |
| 5,061,275 | 10/1991 | Wallsten et al. . |
| 5,062,829 | 11/1991 | Pryor et al. . |
| 5,064,435 | 11/1991 | Porter . |
| 5,071,407 | 12/1991 | Termin et al. . |
| 5,078,720 | 1/1992 | Burton et al. . |
| 5,078,726 | 1/1992 | Kreamer . |
| 5,078,736 | 1/1992 | Behl . |
| 5,084,065 | 1/1992 | Weldon et al. . |
| 5,089,005 | 2/1992 | Harada . |
| 5,089,006 | 2/1992 | Stiles . |
| 5,092,877 | 3/1992 | Pinchuk . |
| 5,100,429 | 3/1992 | Sinofsky et al. . |
| 5,102,417 | 4/1992 | Palmaz . |
| 5,104,404 | 4/1992 | Wolff . |
| 5,108,416 | 4/1992 | Ryan et al. . |
| 5,108,417 | 4/1992 | Sawyer . |
| 5,116,318 | 5/1992 | Hillstead . |
| 5,116,360 | 5/1992 | Pinchuk et al. . |
| 5,116,365 | 5/1992 | Hillstead . |
| 5,122,154 | 6/1992 | Rhodes . |
| 5,123,917 | 6/1992 | Lee . |
| 5,133,732 | 7/1992 | Wiktor . |
| 5,135,536 | 8/1992 | Hillstead . |
| 5,156,619 | 10/1992 | Ehrenfeld . |
| 5,161,547 | 11/1992 | Tower . |
| 5,163,951 | 11/1992 | Pinchuk et al. . |
| 5,163,952 | 11/1992 | Froix . |
| 5,163,958 | 11/1992 | Pinchuk . |
| 5,171,262 | 12/1992 | MacGregor . |
| 5,183,085 | 2/1993 | Timmermans . |
| 5,192,297 | 3/1993 | Hull . |
| 5,192,307 | 3/1993 | Wall . |
| 5,192,311 | 3/1993 | King et al. . |
| 5,195,984 | 3/1993 | Schatz . |
| 5,197,977 | 3/1993 | Hoffman, Jr. et al. . |
| 5,197,978 | 3/1993 | Hess . |
| 5,234,457 | 8/1993 | Andersen . |
| 5,236,446 | 8/1993 | Dumon . |

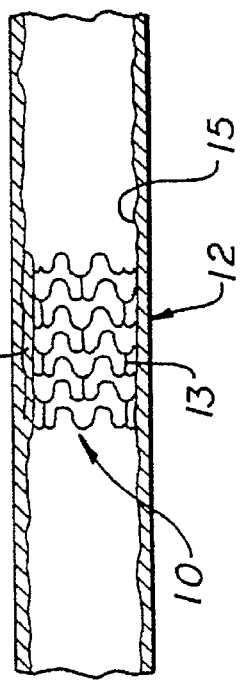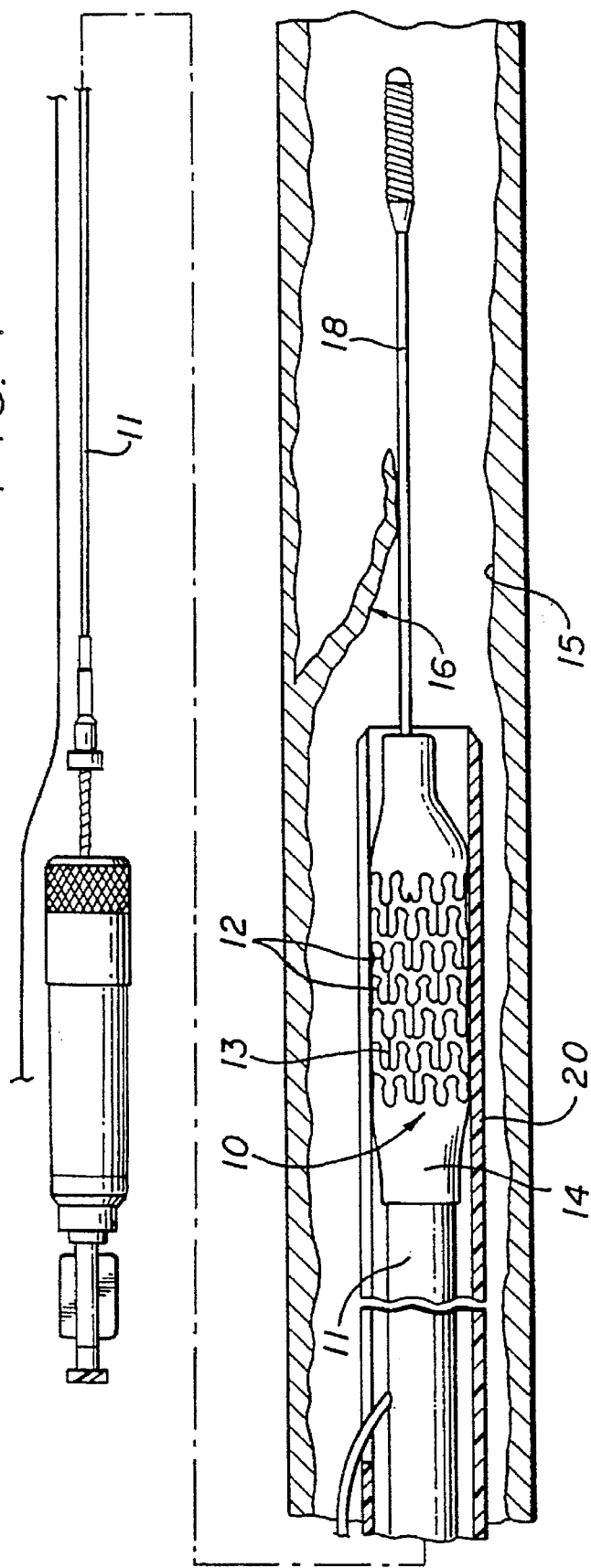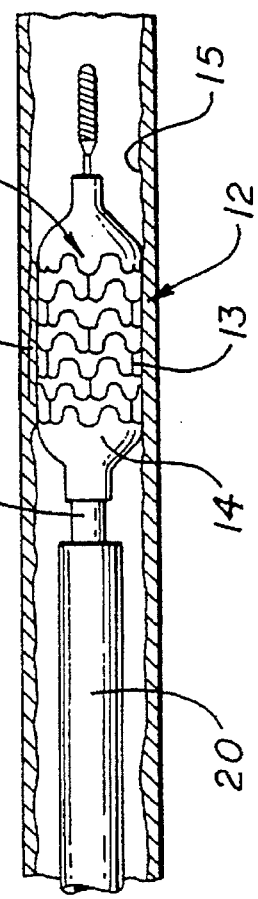

EXPANDABLE STENTS AND METHOD FOR MAKING SAME

This is a division of application Ser. No. 08/454,599, filed May 31, 1995, now U.S. Pat. No. 5,569,295, which is a continuation of U.S. Ser. No. 08/396,886 filed Mar. 1, 1995 (abandoned), which is a continuation of U.S. Ser. No. 08/175,214 filed Dec. 28, 1993 (abandoned).

BACKGROUND OF THE INVENTION

This invention relates to expandable endoprosthesis devices, generally called stents, which are adapted to be implanted into a patient's body lumen, such as blood vessel, to maintain the patency thereof. These devices are useful in the treatment and repair of atherosclerotic stenoses in blood vessels.

Stents are generally cylindrically shaped devices which function to hold open and sometimes expand a segment of a blood vessel or other anatomical lumen. They are particularly suitable for use to support and hold back a dissected arterial lining which can occlude the fluid passageway therethrough.

A variety of devices are known in the art for use as stents and have included coiled wires in a variety of patterns that are expanded after placed intraluminally on a balloon catheter; helically wound coiled springs manufactured from an expandable heat sensitive metal; and self expanding stents inserted in a compressed state and shaped in a zig zag pattern. One of the difficulties encountered using prior stents involved maintaining the radial rigidity needed to hold open a body lumen while at the same time maintaining the longitudinal flexibility of the stent to facilitate its delivery.

Another problem area has been the limiting range of expandability. Certain prior art stents expand only to a limited degree due to the uneven stresses created upon the stents during radial expansion. This necessitates stents with a variety of diameters, thus increasing the cost of manufacture. Additionally, having a stent with a wider range of expandability allows the physician to redilate the stent if the original vessel size was miscalculated.

Another problem with the prior art stents has been contraction of the stent along its longitudinal axis upon radial expansion of the stent. This can cause placement problems within the artery during expansion.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

What has been needed and heretofore unavailable is a stent which has a high degree of flexibility so that it can be advanced through tortuous passageways and can be radially expanded over a wide range of diameters with minimal longitudinal contraction and yet have the mechanical strength to hold open the body lumen into which it is expanded. The present invention satisfies this need.

SUMMARY OF THE INVENTION

The present invention is directed to an expandable stent having a configuration which permits the stent to expand radially to much larger diameters than heretofore were available. The stent is relatively flexible along its longitudinal axis to facilitate delivery through tortuous body lumens, but is stable enough radially, in an expanded condition, to maintain the patency of a body lumen such as an artery or other vessel when implanted therein.

The stent of the present invention generally includes a plurality of adjacent cylindrical elements which are independently expandable in the radial direction and arranged in alignment along a longitudinal stent axis. The cylindrical elements are formed in an irregular serpentine wave pattern transverse to the longitudinal axis and containing a plurality of alternating peaks and valleys. At least one interconnecting member extends between adjacent cylindrical elements and connects them to one another. These are connected to insure a minimal longitudinal contraction during expansion. The irregular serpentine pattern contains varying degrees of curvature in regions of the peaks and valleys and is adapted so that radial expansion of said cylindrical elements is generally uniform around their circumferences during expansion of the stent from its contracted condition to its expanded condition.

The resulting stent structure is a series of radially expandable cylindrical elements which are spaced longitudinally close enough so that small dissections in the wall of a body lumen may be pressed back into position against the lumenal wall, but not so close as to compromise the longitudinal flexibility of the stent. The irregular serpentine pattern allows for an even expansion around the circumference by accounting for the relative differences in stress created by the radial expansion of the cylindrical elements. The individual cylindrical elements may rotate slightly relative to adjacent cylindrical elements without significant deformation, cumulatively providing a stent which is flexible along its length and about its longitudinal axis, but which is still very stable in the radial direction in order to resist collapse.

The stent embodying features of the invention can be readily delivered to the desired lumenal location by mounting it on an expandable member of a delivery catheter, for example a balloon, and passing the catheter-stent assembly through the body lumen to the implantation site. A variety of means for securing the stent to the expandable member on the catheter for delivery to the desired location is available. It is presently preferred to compress the stent onto the balloon. Other means to secure the stent to the balloon include providing ridges or collars on the inflatable member to restrain lateral movement, or using bioabsorbable temporary adhesives.

The presently preferred structure for the expandable cylindrical elements which form the stent of the present invention generally have a circumferential serpentine pattern containing a plurality of alternating peaks and valleys. The degrees of curvature along adjacent peaks and valleys are different in order to compensate for the stresses created during expansion of the stent so that expansion of each of the peaks and valleys is uniform relative to one another. This novel structure permits the stent to radially expand from a first smaller diameter to any number of second larger diameters since stress is distributed more uniformly along the pattern. This uniformity in stress distribution reduces the tendency of stress fractures in one particular region and allows higher expansion rates. The structure also allows the stent to expand to a greater radial expansion than heretofore was available without loss of radial strength and limited contraction of longitudinal length. The open reticulated structure of the stent allows for the perfusion of blood over a large portion of the arterial wall which can improve the healing and repair of a damaged arterial lining.

The irregular serpentine pattern has different degrees of curvature of adjacent peaks and valleys which compensates for the expansive properties of the peaks and valleys. Additionally, the degree of curvature along the peaks is different in immediately adjacent areas to compensate for the expansive properties of the valleys adjacent to it. The more even radial expansion of this design results in a stent which can be expanded to a much higher diameter with minimal out of plane twisting since the high stresses are not concentrated in any one particular region of the pattern, but are more evenly distributed among the peaks and valleys, allowing them to expand uniformly. Reducing the amount of out of plane twisting also minimizes the potential for aggravating thrombus formation. Preferably, the serpentine pattern of the individual cylindrical elements are in phase which each other in order to prevent the contraction of the stent along its length when it is expanded. The cylindrical elements of the stent are plastically deformed when expanded (except with NiTi alloys) so that the stent will remain in the expanded condition and therefore they must be sufficiently rigid when expanded to prevent the collapse thereof in use. With super-elastic nickel-titanium (NiTi) alloys, the expansion occurs when the stress of compression is removed so as to allow the phase transformation from austenite back to martensite and as a result the expansion of the stent.

After the stent is expanded some of the peaks and/or valleys may tip outwardly and embed in the vessel wall. Thus, after expansion, the stent does not have a smooth outer wall surface, rather it has projections which embed in the vessel wall and aid in retaining the stent in place in the vessel after expansion.

The elongated interconnecting members which interconnect adjacent cylindrical elements should have a transverse cross-section similar to the transverse dimensions of the undulating components of the expandable cylindrical members. The interconnecting members may be formed in a unitary structure with the expandable cylindrical elements from the same intermediate product, such as a tubular element, or they may be formed independently and mechanically securing the ends of the interconnecting members to the expandable cylindrical elements. Preferably, all of the interconnecting members of a stent are joined at the valleys of the serpentine pattern of adjacent cylindrical elements which form the stent with the serpentine pattern of the cylindrical elements being in phase with one another. In this manner there is limited longitudinal shortening of the stent upon radial expansion when measured from the cylindrical elements at opposite ends of the stent.

The number and location of interconnecting members can be varied in order to develop the desired longitudinal flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

In a presently preferred embodiment of the invention the stent is conveniently and easily formed by coating a stainless steel hypotube with a material resistant to chemical etching, removing portions of the coating to expose portions of underlying tubing which are to be removed to develop the desired stent structure. The exposed portions of the tubing are removed by chemically etching from the tubing exterior leaving the coated portion of the tubing material in the desired pattern of the stent structure. The etching process develops smooth openings in the tubing wall without burrs or other artifacts which are characteristic of mechanical or laser machining processes in the small sized products contemplated. Moreover, a computer controlled laser patterning process to remove the chemical resistive coating makes photo-lithography technology adaptable to the manufacture of these small products. The forming of a mask in the extremely small sizes needed to make the small stents of the invention would be a most difficult task. A plurality of stents can be formed from one length of hypotube by repeating the stent pattern and providing small webs or tabs to interconnect the stents. After the etching process, the stents can be separated by severing the small webs or tabs which connect them.

Other features and advantages of the present invention will become more apparent from the following detailed description of the invention, when taken in conjunction with the accompanying exemplary drawings.

BRIEF DESCRIPTION OF THE DRAWING

FIG. 1 is an elevational view, partially in section, depicting a stent embodying features of the invention which is mounted on a delivery catheter and disposed within a damaged vessel.

FIG. 2 is an elevational view, partially in section, similar to that shown in FIG. 1, wherein the stent is expanded within an damaged vessel, pressing the damaged lining against the vessel wall.

FIG. 3 is an elevational view, partially in section, showing the expanded stent within the vessel after withdrawal of the delivery catheter.

DETAILED DESCRIPTION OF THE INVENTION

Figure 4:
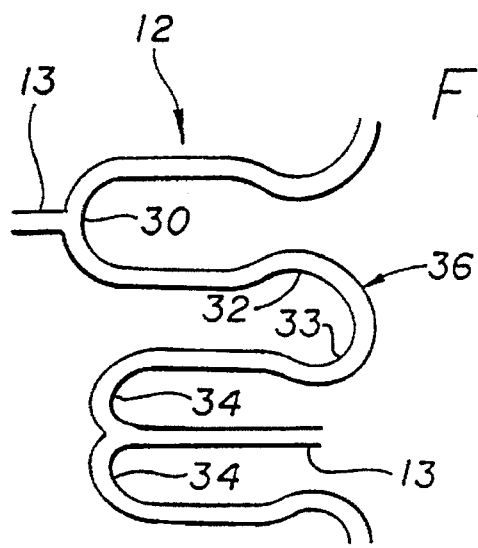
FIG. 4 is an enlarged partial view of the stent of FIG. 5 depicting the irregular serpentine pattern along the peaks and valleys that form the cylindrical elements of the invention.

FIG. 1 illustrates a stent 10 incorporating features of the invention which is mounted onto a delivery catheter 11. The stent generally comprises a plurality of radially expandable cylindrical elements 12 disposed generally coaxially and interconnected by members 13 disposed between adjacent cylindrical elements. The delivery catheter 11 has an expandable portion or balloon 14 for expanding of the stent 10 within an artery 15 or other vessel. The artery 15, as shown in FIG. 1, has a dissected lining 16 which has occluded a portion of the arterial passageway.

The delivery catheter 11 onto which the stent 10 is mounted, is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn, manufactured by the Polymer Products Division of the Du Pont Company. Other polymers may also be used. In order for the stent 10 to remain in place on the balloon 14 during delivery to the site of the damage within the artery 15, the stent 10 is compressed onto the balloon. A retractable protective delivery sleeve 20 may be provided to further ensure that the stent stays in place on the expandable portion of the delivery catheter 11 and prevent abrasion of the body lumen by the open surface of the stent 10 during delivery to the desired arterial location. Other means for securing the stent 10 onto the balloon 14 may also be used, such as providing collars or ridges on the ends of the working portion, i.e., the cylindrical portion, of the balloon.

Each radially expandable cylindrical element 12 of the stent 10 may be independently expanded, therefore the balloon 14 may be provided with an inflated shape other than cylindrical, e.g., tapered, to facilitate implantation of the stent 10 in a variety of body lumen shapes.

In a preferred embodiment, the delivery of the stent 10 is accomplished in the following manner. The stent 10 is first mounted onto the inflatable balloon 14 on the distal extremity of the delivery catheter 11. The stent may be "crimped" down onto the balloon to ensure a low profile. The catheter-stent assembly can be introduced within the patient's vasculature in a conventional Seldinger technique through a guiding catheter (not shown). A guidewire 18 is disposed across the damaged arterial section with the detached or dissected lining 16 and then the catheter-stent assembly is advanced over a guidewire 18 within the artery 15 until the stent 10 is directly under the detached lining 16. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent 10 from an elongated tubular member, the undulating component of the cylindrical elements of the stent 10 is relatively flat in transverse cross-section, so that when the stent is expanded, the cylindrical elements are pressed into the wall of the artery 15 and as a result do not interfere with the blood flow through the artery 15. The cylindrical elements 12 of stent 10 which are pressed into the wall of the artery 15 will eventually be covered with endothelial cell growth which further minimizes blood flow interference. The serpentine pattern of the cylindrical sections 12 provide good tacking characteristics to prevent stent movement within the artery. Furthermore, the closely spaced cylindrical elements 12 at regular intervals provide uniform support for the wall of the artery 15, and consequently are well adapted to tack up and hold in place small flaps or dissections in the wall of the artery 15 as illustrated in FIGS. 2 and 3.

Figure 5:
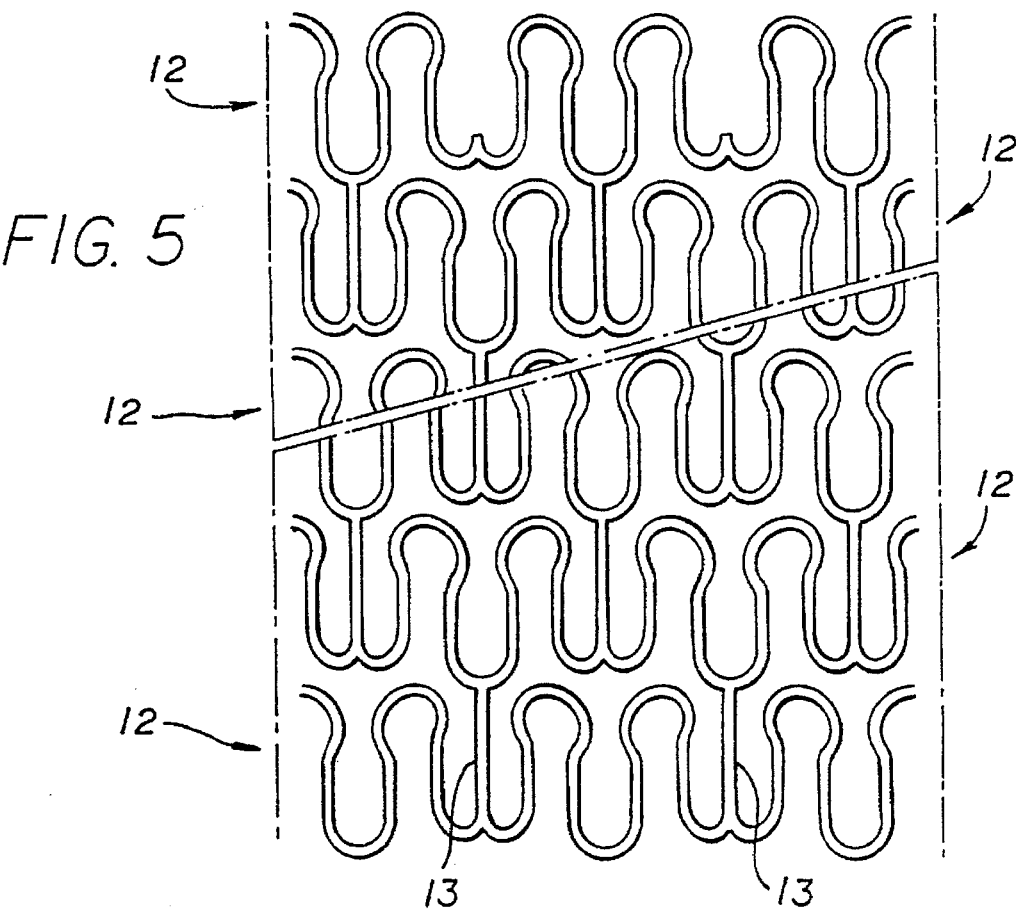
FIG. 5 is a plan view of a flattened section of a stent of the invention which illustrates the irregular serpentine pattern of the stent.
Figure 7:
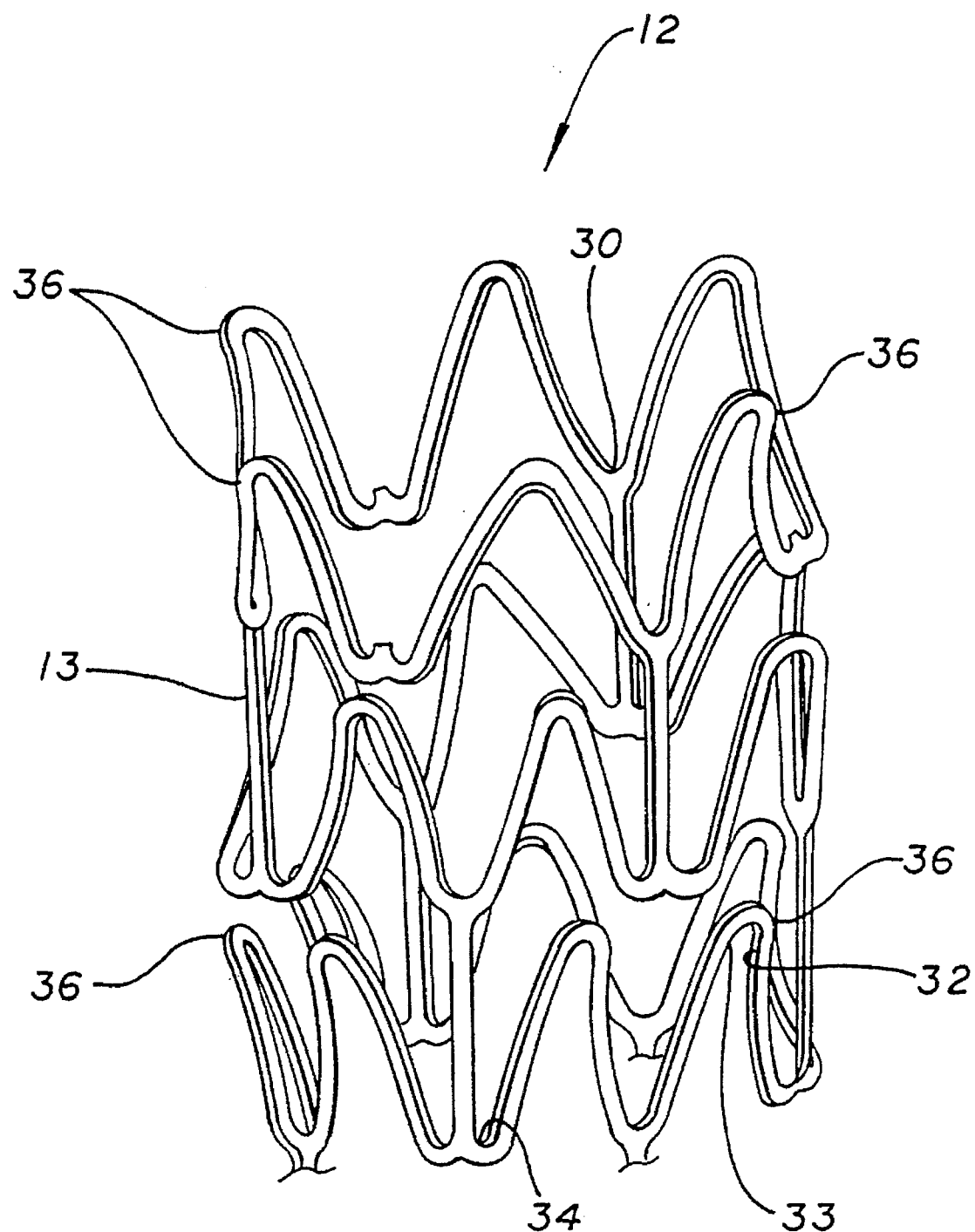
FIG. 7 is a view of the stent in an expanded condition.

In the preferred embodiment, as depicted in FIGS. 4 and 5, the stresses involved during expansion from a low profile to an expanded profile are much more evenly distributed among the various peaks and valleys. As seen in FIG. 4, a portion of cylindrical element 12 of stent 10 illustrates the irregular serpentine pattern having a plurality peaks and valleys which aids in the even distribution of expansion forces. Interconnecting members 13 serve to connect adjacent valleys of cylindrical element 12 as described above.

During expansion, the portion 34 located in the region of the valley where interconnecting member 13 is connected, is the stiffest structure during deformation and the peak portion 36 the least stiff. Thus, a larger radius at portion 34 allows it to begin expanding sooner and at a more uniform rate as compared to the expansion of peak portion 36.

Because of their design, portion 34 is the stiffest structure and peak portion 36 is the least stiff structure, which accounts for the different stresses arising during expansion. Also, the least stiff structure, peak portion 36, is positioned between portion 34 and valley portion 30 which are stiffer structures. To even out the stresses, peak portion 36 has different curvatures at regions 32 and 33. Region 32 has a larger radius than region 33 and will expand more easily. Since region 33 is adjacent the stiffer area of portion 34, both region 33 and portion 34 will expand more uniformly and more evenly distribute the expansion stresses. Further, valley portion 30 and portion 34 also have a larger diameter to even out the expansion forces in relation to peak portion 36. Due to the novel structure as described, the shortcomings of the prior art, which include out of plane twisting of the metal, is avoided. These differing degrees of curvature along the peak portion 36 allow for the more even expansion of the cylindrical element 12 as a whole. Additionally, valley portion 34 can have differing degrees of curvature to compensate for the different stress levels during expansion. After expansion, portions of the various elements will turn outwardly, forming small projections which will embed in the vessel wall. For example, the tip of peak portion 36 tips outwardly upon expansion a sufficient amount to embed into the vessel wall and help secure the implanted stent. Upon expansion, the projecting peak 36 provides an outer wall surface on the stent that is not smooth, but instead has a plurality of projecting peaks 36 all along the outer wall surface. While the projections assist in securing the stent in the vessel wall, they are not sharp so as to cause trauma or damage to the vessel wall.

One important feature of the present invention is the capability of the stent to expand from a low-profile diameter to a diameter much greater than heretofore was available, while still maintaining structural integrity in its expanded state. Due to its novel structure, the stent of the present invention has an overall expansion ratio of 1 up to about 4.0 using certain compositions of stainless steel. For example, a 316L stainless steel stent of the invention can be radially expanded from a diameter of 1 unit up to a diameter of about 4.0 units, which deforms the structural members beyond their elastic limits. The stent still retains its structural integrity in the expanded state and it serves to hold open the vessel in which it is implanted. Materials other than stainless steel (316L) may give higher or lower expansion ratios without sacrificing structural integrity.

The stent 10 of the present invention can be made in many ways. One method of making the stent is to coat a thin-walled tubular member, such as a stainless steel hypotube, with a material which is resistive to chemical etchants, remove portions of the coating to expose underlying hypotubing which is to be removed, but leave coated portions of the hypotubing in the desired pattern for the stent so that subsequent etching will remove the exposed portions of the metallic tubing. The coated portion of the metallic tube is in the desired shape of the stent. An etching process avoids the necessity of removing burrs or slag inherent in conventional or laser machining processes. It is preferred to remove the etchant-resistive material by means of a machine-controlled laser as illustrated schematically in FIG. 6.

A coating is applied to a length of tubing which, when cured, is resistive to chemical etchants. "Blue Photoresist"

made by the Shipley Company in San Jose, Calif., is an example of suitable commercially available photo-lithographic coatings. The coating is preferably applied by electrophoretic deposition.

To ensure that the surface finish is reasonably uniform, one of the electrodes used for the electrochemical polishing is a doughnut-shaped electrode which is placed about the central portion of the tubular member.

The tubing may be made of suitable biocompatible material such as stainless steel, titanium, tantalum, super-elastic NiTi alloys and even high strength thermoplastic polymers. The stent diameter is very small, so the tubing from which it is made must necessarily also have a small diameter. For PCTA applications, typically the stent has an outer diameter on the order of about 0.065 inch in the unexpanded condition, the same outer diameter of the hypotubing from which it is made, and can be expanded to an outer diameter of 0.2 inch or more. The wall thickness of the hypotubing is about 0.003 inch. For stents implanted in other body lumens, such as PTA applications, the dimensions of the hypotubing are correspondingly larger.

In the instance when the stent is made from plastic, it may have to be heated within the arterial site where the stent is expanded to facilitate the expansion of the stent. Once expanded, it would then be cooled to retain its expanded state. The stent may be conveniently heated by heating the fluid within the balloon or the balloon directly by a known method. The stent may also be made of materials such as super-elastic NiTi alloys. In this case the stent would be formed full size but deformed (e.g. compressed) into a smaller diameter onto the balloon of the delivery catheter to facilitate transfer to a desired intraluminal site. The stress induced by the deformation transforms the stent from a martensite phase to austenite phase and upon release of the force, when the stent reaches the desired intraluminal location, allows the stent to expand due to the transformation back to the martensite phase.

Figure 6:
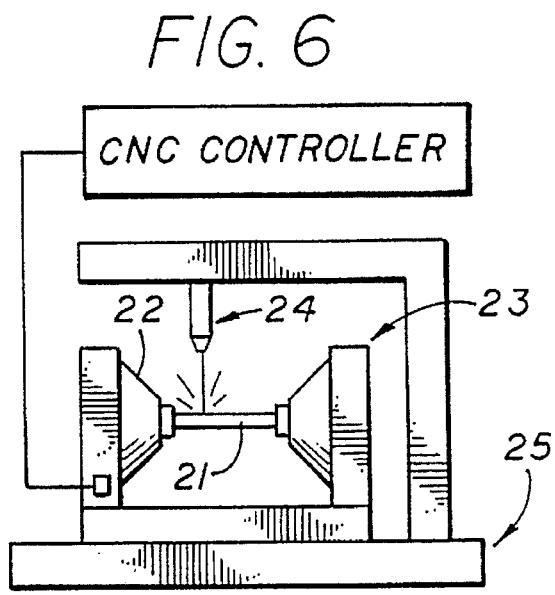
FIG. 6 is a schematic representation of equipment for selectively removing coating applied to tubing in the manufacturing of the stents of the present invention.

Referring to FIG. 6, the coated tubing 21 is put in a rotatable collet fixture 22 of a machine controlled apparatus 23 for positioning the tubing 21 relative to a laser 24.

According to machine-encoded instructions, the tubing 21 is rotated and moved longitudinally relative to the laser 24 which is also machine controlled. The laser selectively removes the etchant-resistive coating on the tubing by ablation and a pattern is formed such that the surface of the tube that is to be removed by a subsequent chemical etching process is exposed. The surface of the tube is therefore left coated in the discrete pattern of the finished stent.

One system for removing the coating on the tubing includes the use of an 80 watt $CO_2$ laser, such as a Coherent Model 44, in pulse mode (0.3 ms pulse length); 48 ma key current and 48 W key power with 0.75 W average power; at 100 Hz; Anorad FR=20; 12.5 Torr; with no assist gas. Another system for removing the coating on the tubing includes the use of the same laser only operating in the Q switched mode, generating about 1.6 kilohertz for approximately 500 nanosecond intervals (i.e., mechanically chopping the beam). Low pressure air is directed through the fine focus head to ensure that no vapor contacts the lens. The assist gas jet assembly on the laser unit may be removed to allow a closer proximity of the fine focus head and the collet fixture. Optimum focus is set at the surface of the tubing. Cured photoresist coating readily absorbs the energy of the $CO_2$ wavelength, so that it can be readily removed by the laser. The process of photoresist ablation with the laser still leaves a very thin film of photo-resist which must be removed. Known methods of removal such as plasma etching, can be used to remove the photo-resist film. For manufacturing efficiency a coated four-inch length of 0.06 inch stainless steel tubing is preferred and four stents can be patterned on the length of tubing. Three tabs or webs between stents provide good handling characteristics for the tubing after the etching process. It is also possible to use a YAG, excimer or ion laser in place of a $CO_2$ laser. The settings and power requirements of these other lasers would be different than that described for the $CO_2$.

The process of patterning the resistive coating on the stent is, automated except for loading and unloading the length of tubing. Referring again to FIG. 6 it may be done, for example, using a CNC opposing collet fixture 22 for axial rotation of the length of tubing, in conjunction with a CNC X/Y table 25 to move the length of tubing axially relative to a machine controlled laser as described. The entire space between collets can be patterned using the $CO_2$ laser set-up of the forgoing example. The program for control of the apparatus is dependent on the particular configuration used and the pattern to be ablated in the coating, but is otherwise conventional.

This process makes possible the application of present photo-lithography technology in manufacturing the stents. While there is presently no practical way to mask and expose a tubular photoresist coated part of the small size required for making intravascular stents, the foregoing steps eliminate the need for conventional masking techniques.

After the coating is thus selectively ablated, the tubing is removed from the collet fixture 22. Next, wax such as ThermoCote N-4 is heated to preferably just above its melting point, and inserted into the tubing under vacuum or pressure. After the wax has solidified upon cooling, it is reheated below its melting point to allow softening, and a smaller diameter stainless steel shaft is inserted into the softened wax to provide support. The tubing is then etched chemically in a conventional manner. After cutting the tabs connecting the stents any surface roughness or debris from the tabs is removed. The stents are preferably electrochemically polished in an acidic aqueous solution such as a solution of ELECTRO-GLO #300, sold by the ELECTRO-GLO CO., INC. in Chicago, Ill., which is a mixture of sulfuric acid, carboxylic acids, phosphates, corrosion inhibitors and a biodegradable surface active agent. The bath temperature is maintained at about 110–135 degrees F. and the current density is about 0.4 to about 1.5 amps per $in^2$. Cathode to anode area should be at least about two to one. The stents may be further treated if desired, for example by applying a biocompatible coating. Other methods for forming the stent of the present invention in a manner similar to that just described are well known in the art.

While the invention has been illustrated and described herein in terms of its use as an intravascular stent, it will be apparent to those skilled in the art that the stent can be used in other instances in all vessels in the body. Since the stent of the present invention has the novel feature of expanding to very large diameters while retaining its structural integrity, it is particularly well suited for implantation in almost any vessel where such devices are used. This feature, coupled with limited longitudinal contraction of the stent when it is radially expanded, provides a highly desirable support member for all vessels in the body. Other modifications and improvements may be made without departing from the scope of the invention.

What is claimed is:

1. A longitudinally flexible stent for implanting in a body lumen and expandable from a contracted condition to an expanded condition, comprising:

a plurality of adjacent cylindrical elements each having a circumference extending around a longitudinal stent axis and each element being substantially independently expandable in the radial direction, the cylindrical elements being arranged in alignment along the longitudinal stent axis;

the cylindrical elements formed in a generally serpentine wave pattern transverse to the longitudinal axis and containing a plurality of alternating peaks and valleys;

at least the peaks having varying radii of curvature, the varying radii of curvature being selected to provide a generally uniform radial expansion of the cylindrical elements;

the peaks on each of the cylindrical elements being substantially aligned in phase along the longitudinal stent axis; and at least one interconnecting member extending between adjacent cylindrical elements and connecting them to one another to form the longitudinally flexible stent.

2. The stent of claim 1, wherein the valleys on each of the cylindrical elements are configured to be substantially in phase along the longitudinal stent axis.

3. The stent of claim 1, wherein the stent is formed from no less than five cylindrical elements aligned on the longitudinal stent axis.

4. A method for implanting a stent in a body lumen, the stent having a first contracted condition and a second expanded condition, a plurality of adjacent cylindrical elements each having a circumference extending around a longitudinal stent axis and each element being expandable in the radial direction, the cylindrical elements being arranged in alignment along the longitudinal stent axis, the cylindrical elements formed in a generally serpentine wave pattern transverse to the longitudinal axis and containing a plurality of alternating peaks and valleys, at least the peaks having varying radii of curvature, the method comprising:

expanding the stent from the first contracted condition to the second expanded condition; and forming a plurality of projecting tips that project radially outwardly from the cylindrical elements as the stent expands from the first contracted condition to the second expanded condition.

5. The method of claim 4, wherein the step of forming the plurality of projecting tips includes forming the projecting tips from the plurality of peaks.

6. The method of claim 4, wherein the step of expanding the stent includes expanding the stent radially outwardly into contact with the body lumen so that the projecting tips are embedded in the body lumen thereby firmly attaching the stent to the body lumen.

7. The method of claim 6, wherein the embedding step includes embedding the projecting tips into a body lumen taken from the group of body lumens including a coronary artery, a peripheral artery, a peripheral vein, a carotid artery, a vein, and an aorta.

8. A catheter and stent assembly for delivering and implanting the stent in a body lumen, comprising:

an elongated catheter having a proximal end and a distal end and a guide wire lumen extending for at least a portion of the catheter;

an elongated guide wire adapted for slidable movement in the guide wire lumen;

an expandable member associated with the catheter distal end and an inflation lumen in the catheter extending from the catheter proximal end into fluid communication with the expandable member;

a stent having a plurality of cylindrical elements along a longitudinal stent axis, the cylindrical elements formed in a generally serpentine wave pattern and containing a plurality of alternating peaks and valleys, the peaks and valleys having varying radii of curvature to ensure uniform expansion of the stent;

the stent being mounted on the expandable member in a first contracted condition and expanded to a second expanded condition upon inflation of the expandable member, thereby implanting the stent in the body lumen.

9. The catheter and stent assembly of claim 8, wherein the catheter guide wire lumen has a side port on an outer surface of the catheter through which the guide wire extends.

10. The catheter and stent assembly of claim 8, wherein a protective sleeve is associated with the catheter so that the sleeve covers the stent during intraluminal delivery and the sleeve is withdrawn to expose the stent during implanting in the body lumen.

* * * * *